US008897850B2

(12) United States Patent
Jochim et al.

(10) Patent No.: US 8,897,850 B2
(45) Date of Patent: Nov. 25, 2014

(54) SENSOR WITH INTEGRATED LIVING HINGE AND SPRING

(75) Inventors: Robert Jochim, Dublin, CA (US); Joseph Coakley, Dublin, CA (US); Robert W. Flagler, Pleasanton, CA (US); Darius Eghbal, Oakland, CA (US); Michael H. Vardanega, Brentwood, CA (US); Donald S. Nelson, San Ramon, CA (US)

(73) Assignee: Covidien LP, Mansfield, MA (US)

( * ) Notice: Subject to any disclaimer, the term of this patent is extended or adjusted under 35 U.S.C. 154(b) by 1440 days.

(21) Appl. No.: 12/345,345

(22) Filed: Dec. 29, 2008

(65) Prior Publication Data

US 2009/0171224 A1    Jul. 2, 2009

Related U.S. Application Data

(60) Provisional application No. 61/009,709, filed on Dec. 31, 2007.

(51) Int. Cl.
*A61B 5/00*    (2006.01)
*A61B 5/1455*    (2006.01)

(52) U.S. Cl.
CPC ............. *A61B 5/6826* (2013.01); *A61B 5/6838* (2013.01); *A61B 5/14552* (2013.01)
USPC ........................................................ 600/344

(58) Field of Classification Search
USPC .................................. 600/310, 322, 323, 344
See application file for complete search history.

(56) References Cited

U.S. PATENT DOCUMENTS 3,721,813 A    3/1973    Condon et al.
4,506,416 A *  3/1985    Ohminato et al. ............ 24/67 R
(Continued)

FOREIGN PATENT DOCUMENTS

DE    3516338    11/1986
DE    3703458    8/1988
(Continued)

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

(Continued)

*Primary Examiner* — Melanie Tyson
(74) *Attorney, Agent, or Firm* — Fletcher Yoder PC

(57) ABSTRACT

Embodiments of the present disclosure relate generally to a sensor assembly. In various embodiments the sensor assembly includes a body having a first segment, a second segment, and a living hinge. The living hinge has a pivot axis and mechanically couples the first segment and the second segment. Further, the living hinge facilitates the first segment and the second segment to pivoting relative to one another about the pivot axis. Embodiments may also relate to a method of manufacturing a sensor frame. The method may include forming an integral sensor body having a first frame segment, a second frame segment, and a living hinge. The first frame segment and the second frame segment are configured to pivot relative to one another about a pivot axis of the living hinge. The method may also include coupling one or more biasing mechanisms to the first frame segment and the second frame segment. The biasing mechanism is configured to generate a moment about the pivot axis of the living hinge. The moment biases the first segment and second segment into a closed position.

29 Claims, 8 Drawing Sheets

(56) References Cited

U.S. PATENT DOCUMENTS

| | | |
|---|---|---|
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,681,109 A * | 7/1987 | Arroyo ..................... 606/158 |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,039 A | 8/1991 | Hattori et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H0001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |

(56) References Cited

U.S. PATENT DOCUMENTS

| | | | |
|---|---|---|---|
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |
| 5,417,207 A | 5/1995 | Young et al. | |
| 5,421,329 A | 6/1995 | Casciani et al. | |
| 5,425,360 A | 6/1995 | Nelson | |
| 5,425,362 A | 6/1995 | Siker et al. | |
| 5,427,093 A | 6/1995 | Ogawa et al. | |
| 5,429,128 A | 7/1995 | Cadell et al. | |
| 5,429,129 A | 7/1995 | Lovejoy et al. | |
| 5,431,159 A | 7/1995 | Baker et al. | |
| 5,431,170 A | 7/1995 | Mathews | |
| 5,437,275 A | 8/1995 | Amundsen et al. | |
| 5,438,986 A | 8/1995 | Disch et al. | |
| 5,448,991 A | 9/1995 | Polson et al. | |
| 5,452,717 A | 9/1995 | Branigan et al. | |
| 5,465,714 A | 11/1995 | Scheuing | |
| 5,469,845 A | 11/1995 | DeLonzor et al. | |
| RE35,122 E | 12/1995 | Corenman et al. | |
| 5,482,034 A | 1/1996 | Lewis et al. | |
| 5,482,036 A | 1/1996 | Diab et al. | |
| 5,483,646 A | 1/1996 | Uchikoga | |
| 5,485,847 A | 1/1996 | Baker, Jr. | |
| 5,490,505 A | 2/1996 | Diab et al. | |
| 5,490,523 A | 2/1996 | Isaacson et al. | |
| 5,491,299 A | 2/1996 | Naylor et al. | |
| 5,494,032 A | 2/1996 | Robinson et al. | |
| 5,497,771 A | 3/1996 | Rosenheimer | |
| 5,499,627 A | 3/1996 | Steuer et al. | |
| 5,503,148 A | 4/1996 | Pologe et al. | |
| 5,505,199 A | 4/1996 | Kim | |
| 5,507,286 A | 4/1996 | Solenberger | |
| 5,511,546 A * | 4/1996 | Hon | 600/490 |
| 5,517,988 A | 5/1996 | Gerhard | |
| 5,520,177 A | 5/1996 | Ogawa et al. | |
| 5,521,851 A | 5/1996 | Wei et al. | |
| 5,522,388 A | 6/1996 | Ishikawa et al. | |
| 5,524,617 A | 6/1996 | Mannheimer | |
| 5,529,064 A | 6/1996 | Rall et al. | |
| 5,533,507 A | 7/1996 | Potratz et al. | |
| 5,551,423 A | 9/1996 | Sugiura | |
| 5,551,424 A | 9/1996 | Morrison et al. | |
| 5,553,614 A | 9/1996 | Chance | |
| 5,553,615 A | 9/1996 | Carim et al. | |
| 5,555,882 A | 9/1996 | Richardson et al. | |
| 5,558,096 A | 9/1996 | Palatnik | |
| 5,560,355 A | 10/1996 | Merchant et al. | |
| 5,564,417 A | 10/1996 | Chance | |
| 5,575,284 A | 11/1996 | Athan et al. | |
| 5,575,285 A | 11/1996 | Takanashi et al. | |
| 5,577,500 A | 11/1996 | Potratz | |
| 5,582,169 A | 12/1996 | Oda et al. | |
| 5,584,296 A | 12/1996 | Cui et al. | |
| 5,588,425 A | 12/1996 | Sackner et al. | |
| 5,588,427 A | 12/1996 | Tien | |
| 5,590,652 A | 1/1997 | Inai | |
| 5,595,176 A | 1/1997 | Yamaura | |
| 5,596,986 A | 1/1997 | Goldfarb | |
| 5,611,337 A | 3/1997 | Bukta | |
| 5,617,852 A | 4/1997 | MacGregor | |
| 5,619,992 A | 4/1997 | Guthrie et al. | |
| 5,626,140 A | 5/1997 | Feldman et al. | |
| 5,630,413 A | 5/1997 | Thomas et al. | |
| 5,632,272 A | 5/1997 | Diab et al. | |
| 5,632,273 A | 5/1997 | Suzuki | |
| 5,634,459 A | 6/1997 | Gardosi | |
| 5,638,593 A | 6/1997 | Gerhardt et al. | |
| 5,638,818 A | 6/1997 | Diab et al. | |
| 5,645,060 A | 7/1997 | Yorkey et al. | |
| 5,645,440 A | 7/1997 | Tobler et al. | |
| 5,660,567 A | 8/1997 | Nierlich et al. | |
| 5,662,105 A | 9/1997 | Tien | |
| 5,662,106 A | 9/1997 | Swedlow et al. | |
| 5,666,952 A | 9/1997 | Fuse et al. | |
| 5,671,529 A | 9/1997 | Nelson | |
| 5,673,692 A | 10/1997 | Schulze et al. | |
| 5,673,693 A | 10/1997 | Solenberger | |
| 5,676,139 A | 10/1997 | Goldberger et al. | |
| 5,676,141 A | 10/1997 | Hollub | |
| 5,678,544 A | 10/1997 | DeLonzor et al. | |
| 5,680,857 A | 10/1997 | Pelikan et al. | |
| 5,685,299 A | 11/1997 | Diab et al. | |
| 5,685,301 A | 11/1997 | Klomhaus | |
| 5,687,719 A | 11/1997 | Sato et al. | |
| 5,687,722 A | 11/1997 | Tien et al. | |
| 5,692,503 A | 12/1997 | Kuenstner | |
| 5,692,505 A | 12/1997 | Fouts | |
| 5,709,205 A | 1/1998 | Bukta | |
| 5,713,355 A | 2/1998 | Richardson et al. | |
| 5,724,967 A | 3/1998 | Venkatachalam | |
| 5,727,547 A | 3/1998 | Levinson et al. | |
| 5,731,582 A | 3/1998 | West | |
| D393,830 S | 4/1998 | Tobler et al. | |
| 5,743,260 A | 4/1998 | Chung et al. | |
| 5,743,263 A | 4/1998 | Baker, Jr. | |
| 5,746,206 A | 5/1998 | Mannheimer | |
| 5,746,697 A | 5/1998 | Swedlow et al. | |
| 5,752,914 A | 5/1998 | DeLonzor et al. | |
| 5,755,226 A | 5/1998 | Carim et al. | |
| 5,758,644 A | 6/1998 | Diab et al. | |
| 5,760,910 A | 6/1998 | Lepper, Jr. et al. | |
| 5,766,125 A | 6/1998 | Aoyagi et al. | |
| 5,766,127 A | 6/1998 | Pologe et al. | |
| 5,769,785 A | 6/1998 | Diab et al. | |
| 5,772,587 A | 6/1998 | Gratton et al. | |
| 5,774,213 A | 6/1998 | Trebino et al. | |
| 5,776,058 A | 7/1998 | Levinson et al. | |
| 5,776,059 A | 7/1998 | Kaestle | |
| 5,779,630 A | 7/1998 | Fein et al. | |
| 5,779,631 A | 7/1998 | Chance | |
| 5,782,237 A | 7/1998 | Casciani et al. | |
| 5,782,756 A | 7/1998 | Mannheimer | |
| 5,782,757 A | 7/1998 | Diab et al. | |
| 5,782,758 A | 7/1998 | Ausec et al. | |
| 5,786,592 A | 7/1998 | Hök | |
| 5,790,729 A | 8/1998 | Pologe et al. | |
| 5,792,052 A | 8/1998 | Isaacson et al. | |
| 5,795,292 A | 8/1998 | Lewis et al. | |
| 5,797,841 A | 8/1998 | DeLonzor et al. | |
| 5,800,348 A | 9/1998 | Kaestle | |
| 5,800,349 A | 9/1998 | Isaacson et al. | |
| 5,803,910 A | 9/1998 | Potratz | |
| 5,807,246 A | 9/1998 | Sakaguchi et al. | |
| 5,807,247 A | 9/1998 | Merchant et al. | |
| 5,807,248 A | 9/1998 | Mills | |
| 5,810,723 A | 9/1998 | Aldrich | |
| 5,810,724 A | 9/1998 | Gronvall | |
| 5,813,980 A | 9/1998 | Levinson et al. | |
| 5,817,008 A | 10/1998 | Rafert et al. | |
| 5,817,009 A | 10/1998 | Rosenheimer et al. | |
| 5,817,010 A * | 10/1998 | Hibl | 600/344 |
| 5,818,985 A | 10/1998 | Merchant et al. | |
| 5,820,550 A | 10/1998 | Polson et al. | |
| 5,823,950 A | 10/1998 | Diab et al. | |
| 5,823,952 A | 10/1998 | Levinson et al. | |
| 5,827,182 A | 10/1998 | Raley et al. | |
| 5,830,135 A | 11/1998 | Bosque et al. | |
| 5,830,136 A | 11/1998 | DeLonzor et al. | |
| 5,830,137 A | 11/1998 | Scharf | |
| 5,839,439 A | 11/1998 | Nierlich et al. | |
| RE36,000 E | 12/1998 | Swedlow et al. | |
| 5,842,979 A | 12/1998 | Jarman et al. | |
| 5,842,981 A | 12/1998 | Larsen et al. | |

(56) References Cited

U.S. PATENT DOCUMENTS

| | | |
|---|---|---|
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |

(56) References Cited

U.S. PATENT DOCUMENTS

| | | | |
|---|---|---|---|
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddart et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 * | 1/2003 | Larson ........................... 600/323 |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |

(56) References Cited

U.S. PATENT DOCUMENTS

| | | |
|---|---|---|
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom et al. |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,257,438 B2 | 8/2007 | Kinast |
| 7,263,395 B2 | 8/2007 | Chan et al. |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |

(56) References Cited

U.S. PATENT DOCUMENTS

| | | |
|---|---|---|
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1* | 4/2005 | Lindekugel ............... 600/344 |
| 2005/0113651 A1 | 5/2005 | Wood et al. |
| 2005/0177034 A1 | 8/2005 | Beaumont |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2007/0027376 A1* | 2/2007 | Todokoro et al. ............ 600/344 |
| 2007/0032709 A1* | 2/2007 | Coakley et al. ............... 600/323 |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073126 A1 | 3/2007 | Raridan, Jr. |
| 2007/0078309 A1 | 4/2007 | Matlock |
| 2007/0078315 A1* | 4/2007 | Kling et al. ............... 600/323 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| EP | 0724860 | 7/1996 |
| EP | 1945099 | 7/2008 |
| FR | 2685865 | 7/1993 |
| JP | 7001273 | 11/1987 |
| JP | 2111343 | 4/1990 |
| JP | 3116260 | 12/1991 |
| JP | 6014906 | 1/1994 |
| JP | 6269430 | 9/1994 |
| JP | 5049625 | 3/1995 |
| JP | 3116259 | 6/1995 |
| JP | 7236625 | 9/1995 |
| JP | 2000237170 | 9/2000 |
| JP | 2003275192 | 9/2003 |
| JP | 2004089546 | 3/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9111137 | 8/1991 |
| WO | WO9502358 | 1/1995 |
| WO | WO9736536 | 10/1997 |
| WO | WO98/57577 | 12/1998 |
| WO | WO9947039 | 9/1999 |
| WO | WO0059374 | 10/2000 |
| WO | WO2005010567 | 2/2005 |
| WO | WO2005010568 | 2/2005 |

OTHER PUBLICATIONS

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leuven, Belgium, May 1998; pp. 387-392.

Ferrell, T.L., et al.; "Medical Telesensors," *SPIE*, vol. 3253, pp. 193-198 (1998).

(56) References Cited

OTHER PUBLICATIONS

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796.

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summ.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

\* cited by examiner

SENSOR WITH INTEGRATED LIVING HINGE AND SPRING

RELATED APPLICATION

This application claims priority from U.S. Patent Application No. 61/009,709 which was filed Dec. 31, 2007 and is incorporated herein by reference in its entirety.

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One such monitoring technique is commonly referred to as pulse oximetry. Pulse oximetry may be used to measure various blood flow characteristics, such as the blood-oxygen saturation of hemoglobin in arterial blood and/or the rate of blood pulsations corresponding to each heartbeat of a patient.

The devices based upon pulse oximetry techniques are commonly referred to as pulse oximeters. Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus deoxygenated hemoglobin in the blood. The amount of light absorbed and/or scattered may then be used to estimate the amount of the oxygen in the tissue using various algorithms.

During use, the performance of a pulse oximetry sensor may rely on there being substantial contact between the surface of the patient's tissue (i.e., skin or nail bed) and the light emitting and detecting sensors. Good contact between the sensor and the tissue helps prevent light from scattering before being detected by the detecting sensor and helps to prevent additional light, i.e., ambient light or other light not emitted by the sensor, from reaching the detector. For example, a sensor may be clipped about a patients finger tip with the emitter placed on the finger nail, and the detector placed on the under side of the finger tip. In this configuration, the sensor should clip about the finger with enough force to eliminate or reduce the gap between the emitter and the finger nail, as well as eliminate the gap between the detector and the underside of the finger tip. By providing a sufficiently tight fit, the emitted light may travel directly through the tissue of the finger and be detected without additional light being introduced or the emitted light being scattered. Further, the sufficiently tight fit may reduce the likelihood of the pulse oximetry sensor moving relative to the patient's tissue and/or falling off of the patient. However, in practice, anatomic variation between individuals may make achieving such a tight fit with good contact difficult using standardized sensor sizes.

SUMMARY

Certain aspects commensurate in scope with the disclosure are set forth below. It should be understood that these aspects are presented merely to provide the reader with a brief summary of certain forms the disclosure might take and that these aspects are not intended to limit the scope of the disclosure. Indeed, the disclosure may encompass a variety of aspects that may not be set forth below.

In accordance with an embodiment, there is provided a sensor assembly. The sensor assembly includes a body having a first segment, a second segment, and a living hinge. The living hinge has a pivot axis and mechanically couples the first segment and the second segment. Further, the living hinge facilitates the first segment and the second segment to pivoting relative to one another about the pivot axis.

In accordance with an embodiment, there is provided a sensor system. The sensor system includes a sensor assembly having a sensor, a sensor frame, and a living hinge. The sensor has a first sensor portion and a second sensor portion. The sensor frame is configured to support the sensor and includes a first body portion and a second body portion. The living hinge mechanically couples the first body portion and the second body portion, such that the first body portion and the second body portion are configured to pivot relative to one another about a pivot axis of the living hinge. The sensor system also includes at least one member configured to generate a moment about the pivot axis of the living hinge and bias a first end of the first body portion and a first end of the second body portion toward one another.

In accordance with an embodiment, there is provided a method of manufacturing a sensor frame. The method includes forming an integral sensor body having a first frame segment, a second frame segment, and a living hinge. The first frame segment and the second frame segment are configured to pivot relative to one another about a pivot axis of the living hinge. The method also includes coupling one or more biasing mechanisms to the first frame segment and the second frame segment. The biasing mechanism is configured to generate a moment about the pivot axis of the living hinge. The moment biases the first segment and second segment into a closed position.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described herein, various embodiments of sensors are provided which are believed to provide good contact and fit for a range of patient anatomies. In general, examples of these sensors, as described herein, include a living hinge. Prior to discussing such sensors in detail, it should be appreciated that such sensors are typically designed for use with a patient monitoring system.

Figure 1:
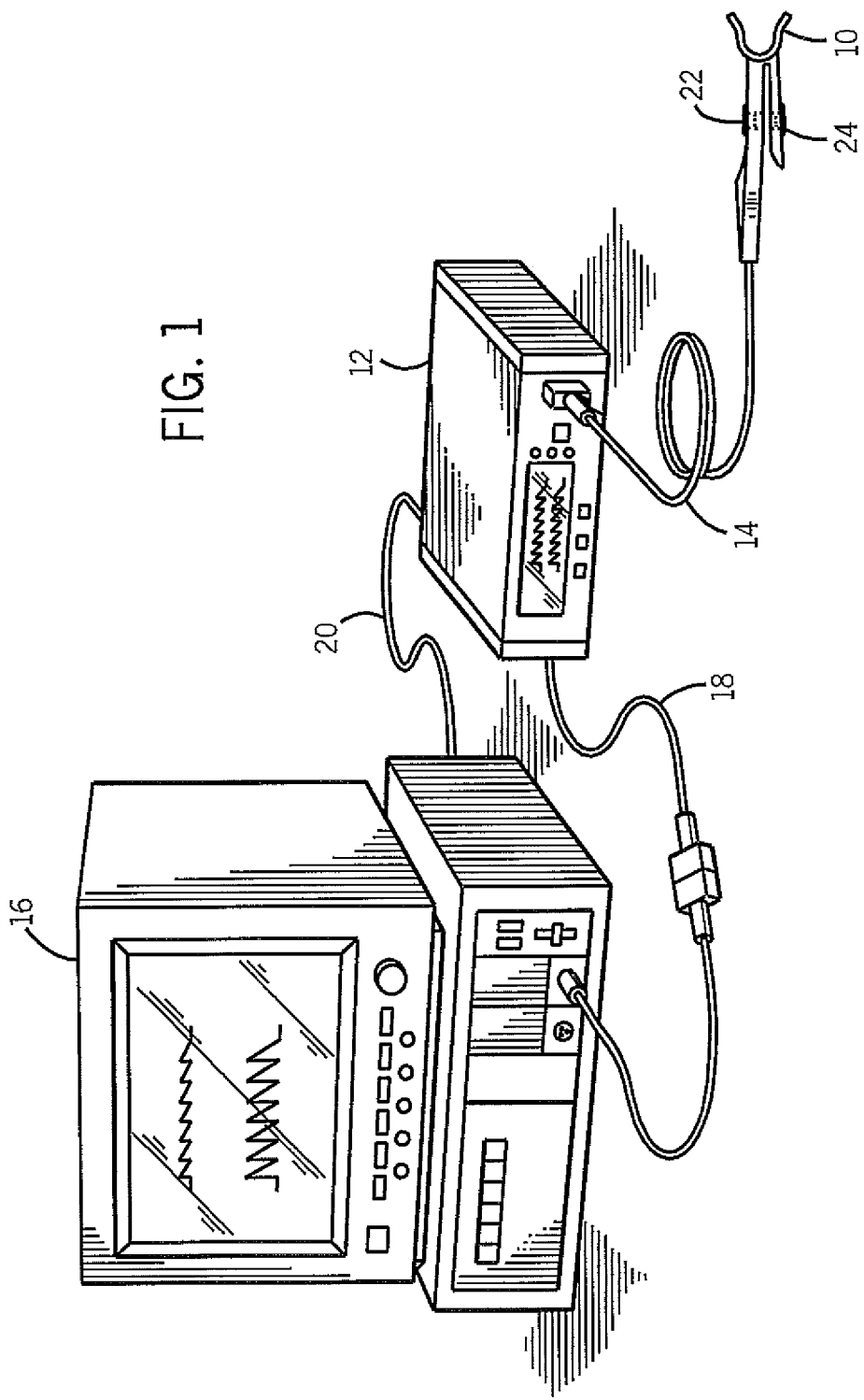
FIG. 1 illustrates a patient monitoring system coupled to a multi-parameter patient monitor and a sensor, in accordance with an embodiment.

Referring now to FIG. 1, a sensor 10 according to an embodiment may be used in conjunction with a patient monitor 12. In the depicted embodiment, a cable 14 connects the sensor 10 to the patient monitor 12. As will be appreciated, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors.

In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or a corresponding wireless transmission) may be used to transmit control or timing signals from the monitor 12 to the sensor 10 and/or to transmit acquired data from the sensor 10 to the monitor 12.

In some embodiments, the cable 14 may be an optical fiber that enables optical signals to be conducted between the patient monitor 12 and the sensor 10.

In an embodiment, the patient monitor 12 may be a suitable pulse oximeter, such as those available from Nellcor Puritan Bennett LLC. In other embodiments, the patient monitor 12 may be a monitor suitable for measuring tissue water fractions, or other body fluid related metrics, using spectrophotometric or other techniques. Furthermore, the patient monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 and to provide additional functions, the patient monitor 12 may be coupled to a multi-parameter patient monitor 16 via a cable 18 connected to a sensor input port and/or a cable 20 connected to a digital communication port.

In an embodiment, the sensor 10, as depicted in FIG. 1, is a clip-style sensor that is overmolded to provide a unitary or enclosed assembly. The sensor 10 may include an emitter 22 and a detector 24 which may be of any suitable type. For example the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and the detector 24 of the sensor 10. The cable 14 may be permanently coupled to the sensor 10, or it may be removably coupled to the sensor 10—the latter alternative being more useful and cost efficient in situations where the sensor 10 is disposable.

In an embodiment, the sensor 10 discussed herein may be configured for either transmission or reflectance type sensing, for example. Furthermore, the sensor 10 may include various structural and functional features designed to facilitate its use. An example of such a sensor and its use and construction may be found in U.S. application Ser. No. 11/199,524 titled "Medical Sensor and Technique for Using the Same" and filed on Aug. 8, 2005, which is hereby incorporated by reference in its entirety for all purposes. As will be appreciated by those of ordinary skill in the art, however, such discussion is merely an example and is not intended to limit the scope of the present technique.

As discussed in greater detail below with regards to FIGS. 2-9, to provide a sufficiently tight fit of the emitter 22 and the detector 24 against the tissue of the patient, certain embodiments of the sensor 10 may include a biasing mechanism, such as a spring, that provides a biasing force to close the distance between the emitter 22 and the detector 24. The spring may also maintain or increase the biasing force as the emitter 22 and detector 24 are spread farther apart from one another. For example, the sensor 10 may include a frame with a top portion that contains the emitter 22 and bottom portion that includes a detector 24, and the frame may take the form of a clip that allows a practitioner to squeeze tabs to separate the emitter 22 and detector 24. The sensor 10 can be opened by a sufficient amount such that the sensor 10 can be clipped to a patient's finger, or to another location on the patient's body. Once attached to the patient, the biasing force may provide resistance to secure and maintain the sensor 10 in contact with the patient's tissue.

Figure 2:
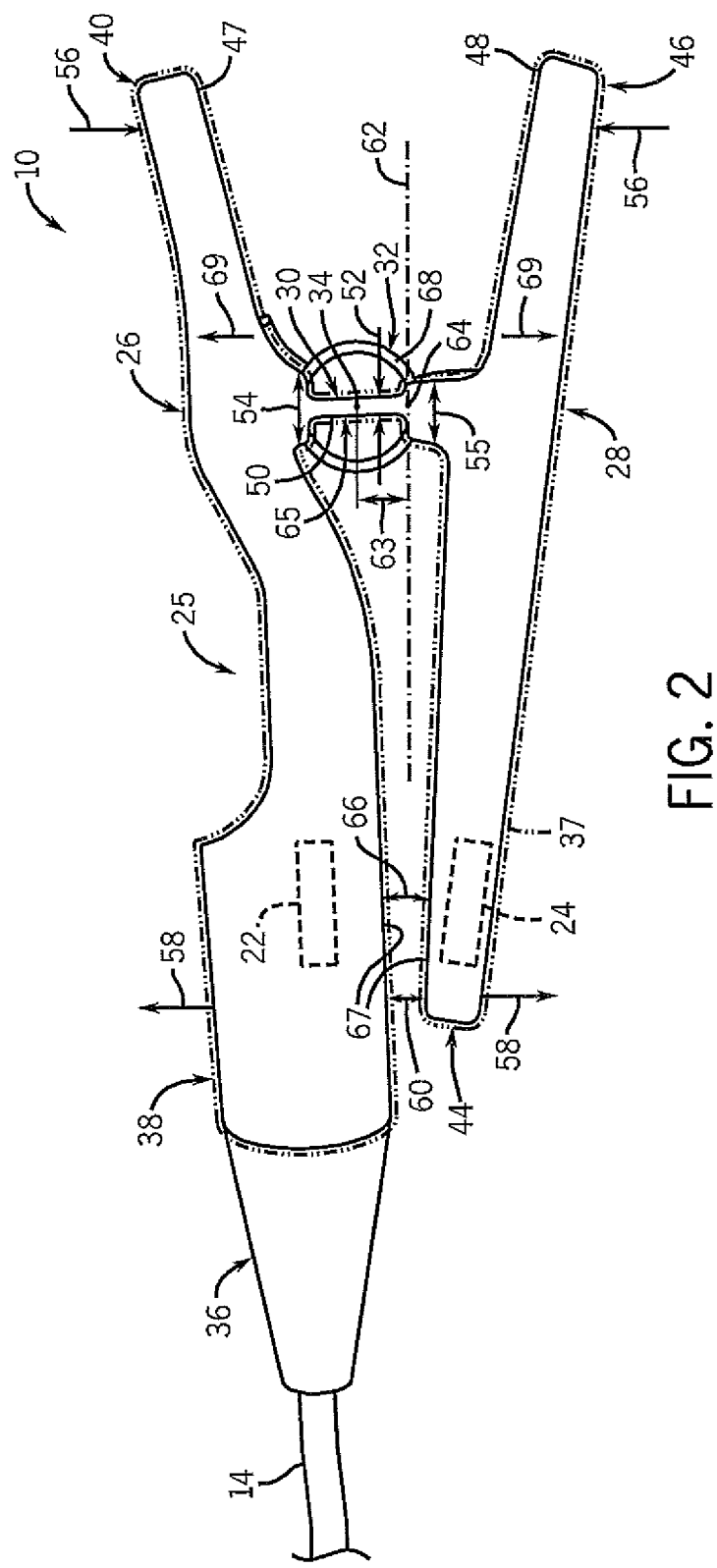
FIG. 2 is a side view of a first embodiment of the sensor having a living hinge, in accordance with an embodiment.

Turning now to FIG. 2, an embodiment of the sensor 10 is illustrated. In the embodiment, the sensor 10 includes a body (e.g., frame) 25 including a first segment 26, a second segment 28, a living hinge 30, and a biasing mechanism 32. The first segment 26 may be coupled to the second segment 28 via the living hinge 30 such that the first segment 26 and the second segment 28 can rotate relative to one another and about a pivot axis 34 of the living hinge 30. In the illustrated embodiment, the sensor 10 may also include a cable connection 36 that couples the cable 14 to the first segment 26 of the sensor 10. The cable connection 36 may include a strain relief, a permanent cabled connection, a quick disconnect mechanism, an overmolded portion of the cable, or the like. Further, the sensor 10 may include overmolding 37. In the illustrated embodiment, the overmolding 37 may encapsulate entirety of the sensor 10. In other embodiments, the overmolding 37 may be affixed to only a portion of the sensor 10.

In an embodiment, the first segment 26 includes a first end 38 and a second end 40. The first end 38 of the first segment 26 may include a first sensing device that is disposed internal to the first segment 26. For example, the emitter 22 of the sensor 10 may be disposed internal to the first end 38 of the first segment 26. The emitter 22 may be mechanically affixed in position via an interference fit, an adhesive, plastic welding, overmolding, or other technique that couples, adheres or holds the emitter 22 to the first segment 26.

In an embodiment, the second segment 28 may include a first end 44 and a second end 46. The first end 44 of the second segment 28 may include a second sensing device that is disposed internal to the second segment 28. For example, the detector 24 of the sensor 10 may be disposed internal to the first end 44 of the second segment 28 and in optical alignment with an emitter 22 disposed in the first segment 26. The detector 24 may be mechanically affixed in position via an interference fit, an adhesive, plastic welding, overmolding, or other technique that couples, attaches or holds the detector 24 to the second segment 28.

The second ends 40 and 46 of the first segment 26 and the second segment 28 may include extensions or tabs that facilitate handling of the sensor 10. For example, in the illustrated embodiment, the second ends 40 and 46 of the sensor 10 include respective protrusions 47 and 48 that extend outward from a location where the living hinge 30 is coupled to the second segment 28. Accordingly, applying squeezing force to the protrusions 47 and 48 to move them toward one another may create a moment about the pivot axis 34 of the living hinge 30. In other words, the protrusions 47 and 48 may act as levers to enable rotation of the first segment 26 and the second segment 28 about the pivot axis 34 of the living hinge 30.

In an embodiment, the first segment 26 and the second segment 28 may be coupled to one another via the living hinge 30. To promote flexure and rotation of the first segment 26 and second segment 28 relative to one another and about the pivot axis 34, the living hinge 30 may, in some embodiments, have a greater tendency to flex than other portions (e.g., the first segment 26 and the second segment 28) of the sensor 10. In certain embodiments, the living hinge 30 includes a necked portion 50 that has a cross-sectional width 52 that is less than the cross-sectional widths 54 and 55 of the components immediately coupled to and adjacent the living hinge 30. In certain embodiments, the first segment 26 and the second segment 28 may include regions proximate the living hinge 30 that have cross sectional widths 54 and 55 that are greater than the cross-sectional width 52 of the living hinge 30. Accordingly, where the living hinge 30, the first segment 26, and the second segment 28 are of similar properties (e.g., mechanical properties), a force applied to the second end 40 of the first segment 26 and/or the second end 46 of the second segment 28 may promote pivoting of the first segment 26 and the second segment 28 about the pivot axis 34. In other words, the living hinge 30 may bend or flex at or near the pivot axis 34 due to the living hinge 30 being a suitable cross sectional width 52 relative to adjacent or nearly adjacent regions.

In an embodiment, applying a force in the direction of arrows 56 to squeeze the second ends 40 and 46 of the first and second segments 26 and 28 together may bend or flex the living hinge 30, enabling the first and second segments 26 and 28 to rotate about the pivot axis 34. In turn, the rotation causes the first ends 38 and 44 to open in the direction of arrows 58, enlarging the gap 60 between the first ends 38 and 44. For example, a medical practitioner may squeeze the second ends 40 and 46 of the sensor 10 to enlarge the gap 60 so that the sensor 10 is in an open position where the first ends 38 and 44 of the sensor 10 can be clipped about a patient's finger, or other location.

In the illustrated embodiment, the pivot axis 34 of the living hinge 30 is offset from a centerline 62 of the sensor 10 by an offset distance 63. The centerline 62 may include a line, axis, or plane that is approximately the same distance from the first segment 26 and the second segment 28 at a referenced location or orientation of the sensor 10. For example, in the illustrated embodiment, the centerline 62 includes a plane that passes through a midpoint 64 of a segment 65 that extends between the first body portion 26 and the second body portion 28. In another embodiment, the centerline 62 may be defined by other features and orientations. For example, in one embodiment, the centerline 62 may be defined by a plane that bisects an angle 66 formed between interior faces 67 of the first end 38 of the first segment 26 and the first end 38 of the second segment 28 when the sensor 10 is closed. In another embodiment, the centerline 62 may include a plane that is approximately equal distance between the interior faces 67 when the sensor 10 is opened such that the faces 67 are parallel to one another.

In an embodiment, offsetting the pivot axis 34 of the living hinge 30 may facilitate manipulating the size and location of the gap 60. For example, increasing the offset distance 63 of the pivot axis 34 may increase the opening angle between the first and second segments 26 and 28 and increase the size of the gap 60 relative to the distance the second ends 40 and 46 are moved (i.e., squeezed) toward one another.

In an embodiment, the recovery of the living hinge 30 may cause the living hinge 30 to have a tendency to return to its unflexed state and, therefore, may provide a restoring (e.g., biasing force) that urges the first segment 26 and the second segment 28 to an unbiased position, such as the opened or closed position. The recovery of the living hinge 30 may be characterized by several mechanical properties, including, but not limited to, the elasticity, stiffness, and/or strength of the material used to form the living hinge 30. In the illustrated embodiment, when the second ends 40 and 46 of the first and second segments 26 and 28 are squeezed to open the sensor 10 (i.e., increase the size of the gap 60), the living hinge 30 may generate a restoring force that resist the bending or flexing of the living hinge 30. Accordingly, when the force applied to open the first and second segments 26 and 28 is reduced, the living hinge 30 may urge the first and second segments 26 and 28 into the closed position (i.e., a position where the size of the gap 60 is reduced). Such a restoring force may enable the sensor 10 to clip and grip to the finger of a patient.

Although the restoring force provided by the living hinge 30 may be sufficient to provide a tight fit with good contact against the patient's tissue, other embodiments may include the addition of a biasing mechanism to provide or increase the restoring force. For example, in the illustrated embodiment, the sensor 10 includes a biasing mechanism 32 disposed between the first segment 26 and the second segment 28. The biasing mechanism 32 may provide a biasing force to cause the first segment 26 and the second segment 28 to rotate relative to one another and reduce the size of the gap 60.

For example, in the illustrated embodiment, the biasing mechanism 32 includes a torsion spring 68 that provides a biasing force in a direction opposite from the direction of the force employed to squeeze the second ends 40 and 46 of the first and second segments 26 and 28 (e.g., a force in the direction of arrows 69). Thus, the biasing mechanism 32 may provide a biasing moment acting on the first and second segments 26 and 28 that urges the sensor 10 to the closed position. As is discussed in further detail below, the biasing mechanism 32 can take a variety of forms, including but not limited to the torsion spring 68, a double torsion spring, a flat spring, a compression spring, a conical compression spring, or combinations thereof. Other embodiments may include one or more of the biasing mechanism 32 coupled to the sensor 10. For example, two biasing mechanisms 32 may be disposed coaxially (i.e., coincident) and abutting one another.

Further, the axis of the biasing mechanism 32 may be coaxial with the pivot axis 34 of the living hinge 30. For example, in the illustrated embodiment, the longitudinal axis of the torsion spring and the pivot axis 34 are coaxial. Locating the axis of the biasing mechanism 32 and the pivot axis 34 coaxial to one another may promote bending and flexing of the living hinge 30 about the pivot axis 34. The axis of the biasing mechanism 32 and the pivot axis 34 may both be offset from the centerline 62 of the sensor 10. For example, as illustrated and discussed above, the axis of the biasing mechanism 32 and the pivot axis 34 may be offset by the offset distance 63 from the centerline 62.

Figure 3:
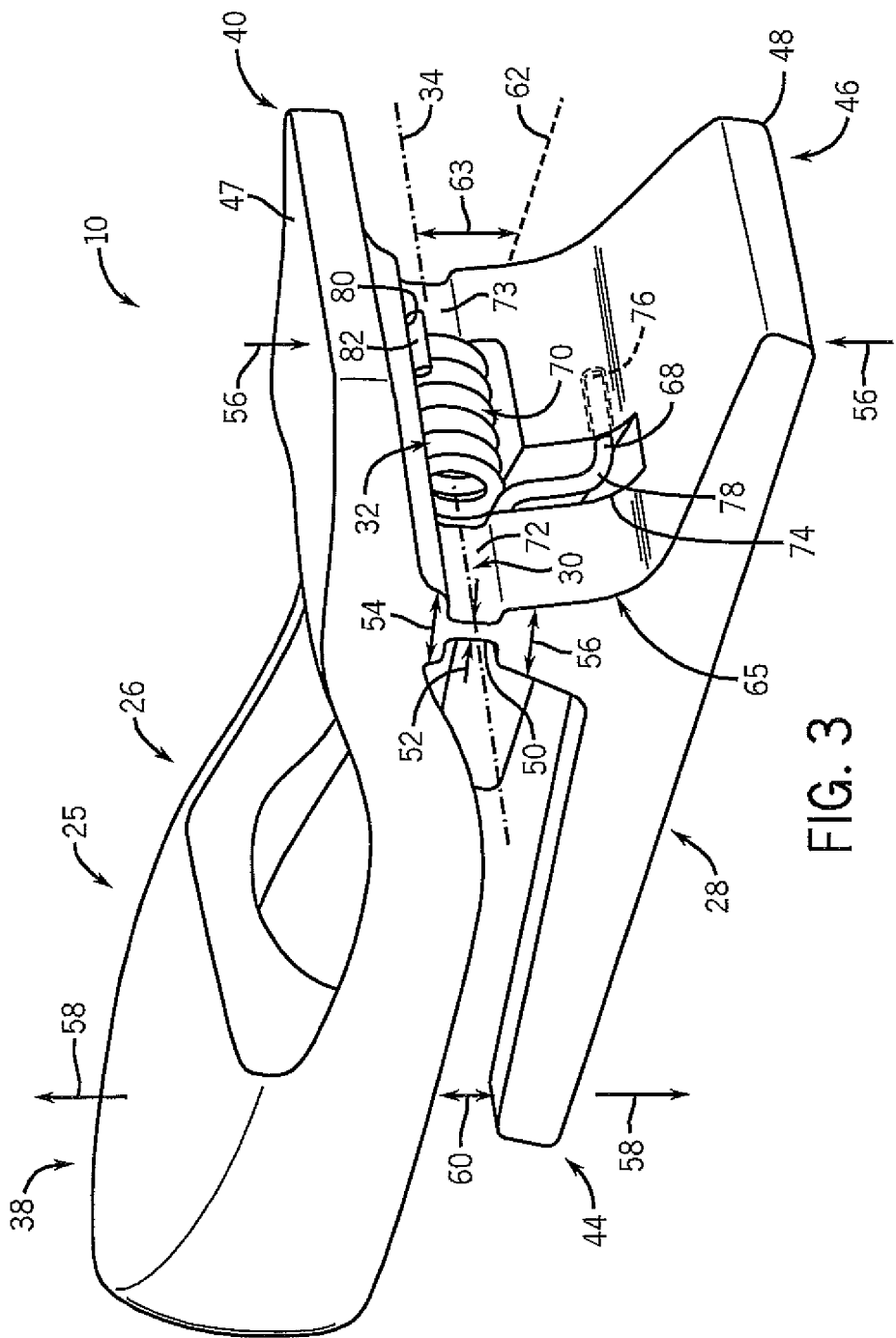
FIG. 3 is a perspective view of the first embodiment of the sensor having a living hinge, in accordance with an embodiment.

Turning now to FIG. 3, a perspective of an embodiment of the sensor 10 including the biasing mechanism 32 is illustrated. The biasing mechanism 32 may include the torsion spring 68 disposed in a slot 70. The slot 70 may include a region void of material, such as a cutout, in a central portion in of the living hinge 30. In such an embodiment, the living hinge 30 is formed from first living hinge portion 72 on one side of the slot 70 and a second living hinge portion 73 on the other side of the slot 70. Further, in the depicted embodiment, the sensor 10 includes indentations that are conducive to the placement and retention of the biasing mechanism 32. For example, a first indentation 74 and a first retaining hole 76 may be formed into the second segment 28. A first leg 78 of the torsion spring 68 may be disposed in the indentation 74 and the retaining hole 76. Similarly, a second indentation 80 may be formed into the first segment 26. A second leg 82 of the torsion spring 68 may be disposed in the second indentation 80. Disposing the first leg 78 into the first indentation 74 and the retaining hole 76 and/or disposing the second leg 82 into the second indentation 80 may facilitate alignment and retention of the torsion spring 68 relative to the living hinge 30.

Figure 4:
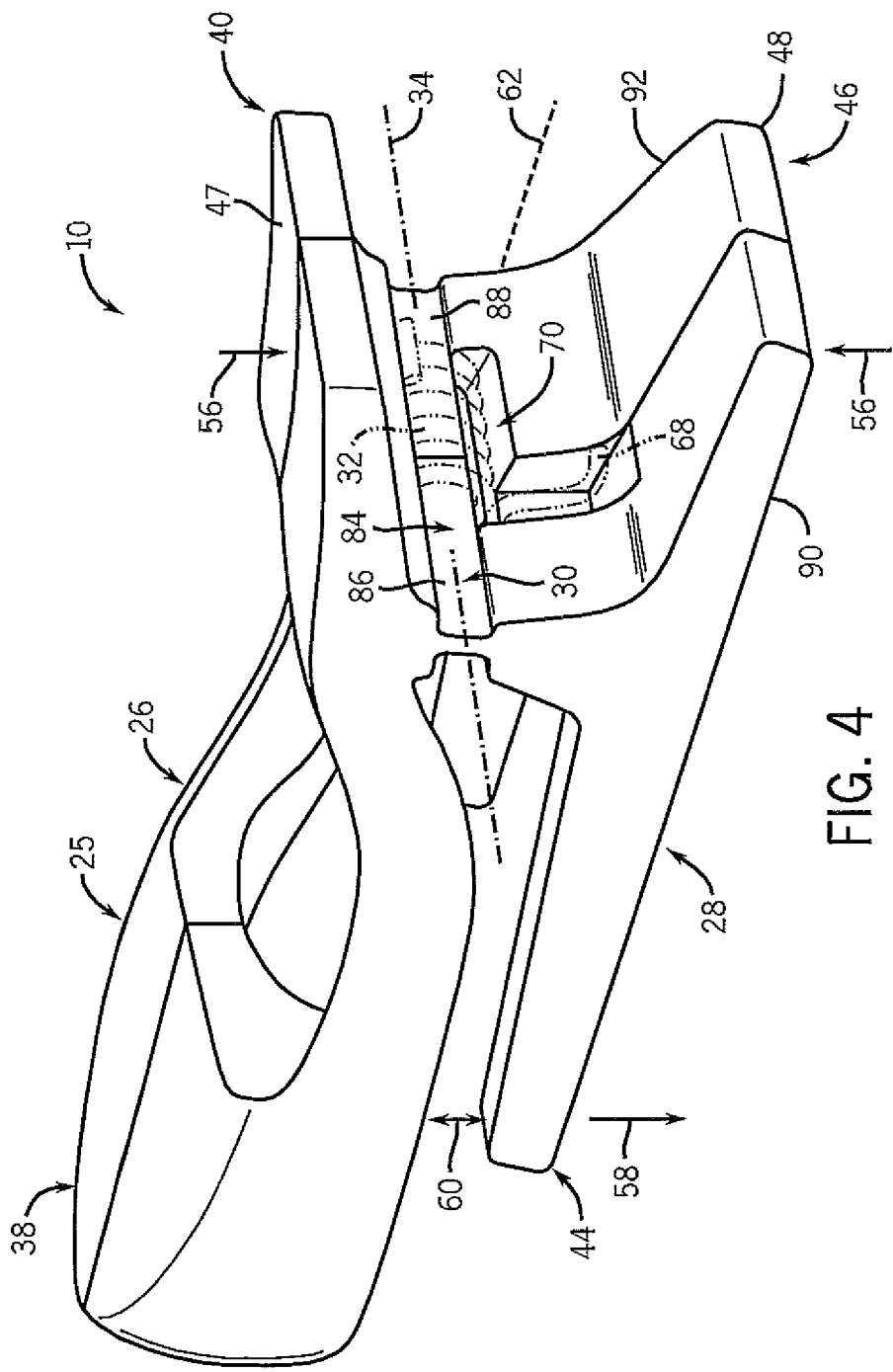
FIG. 4 is a perspective view of a second embodiment of the sensor having a living hinge, in accordance with an embodiment.

Turning now to FIG. 4, a perspective view of an embodiment of the sensor 10 including the biasing mechanism 32 is illustrated. In this embodiment, the biasing mechanism 32 includes the torsion spring 68 disposed in the slot 70 and about a mandrel 84. In the illustrated embodiment, the mandrel 84 includes a portion of material of the sensor 10 extending from the periphery of the slot 70 through the center of the torsion spring 68. The mandrel 84 may extend coaxial with the pivot axis 34 and the axis of the torsion spring 68. The mandrel 84 may facilitate alignment and retention of the biasing mechanism 32 relative to the living hinge 30 during assembly and operation.

In an embodiment, the mandrel 84 may also include features that facilitate assembly of the biasing mechanism 32 to the sensor 10. For example, the mandrel 84 may extend only a portion of the distance across the slot 70 such that the biasing mechanism 32 may be threaded onto the mandrel 84. Further, in the illustrated embodiment, the mandrel 84 includes a first mandrel portion 86 and a second mandrel portion 88 that each extend from opposite sides of the slot 70. In such an embodiment, the sensor 10 may comprise a first sensor portion 90 and a second sensor portion 92 that are assembled to one another to form the sensor 10. The first sensor portion 90 and the second sensor portion 92 can be assembled around the biasing mechanism 32, such that the first mandrel portion 86 and the second mandrel portion 88 extend through the center of the biasing mechanism 32. In the illustrated embodiment, the mandrel 84 includes at least a portion of the living hinge 30. In other embodiments, the mandrel 84 may include a portion of the first segment 26, the second segment 28, or a combination of the first segment 26, the second segment 28 and/or the living hinge 30.

Figure 5:
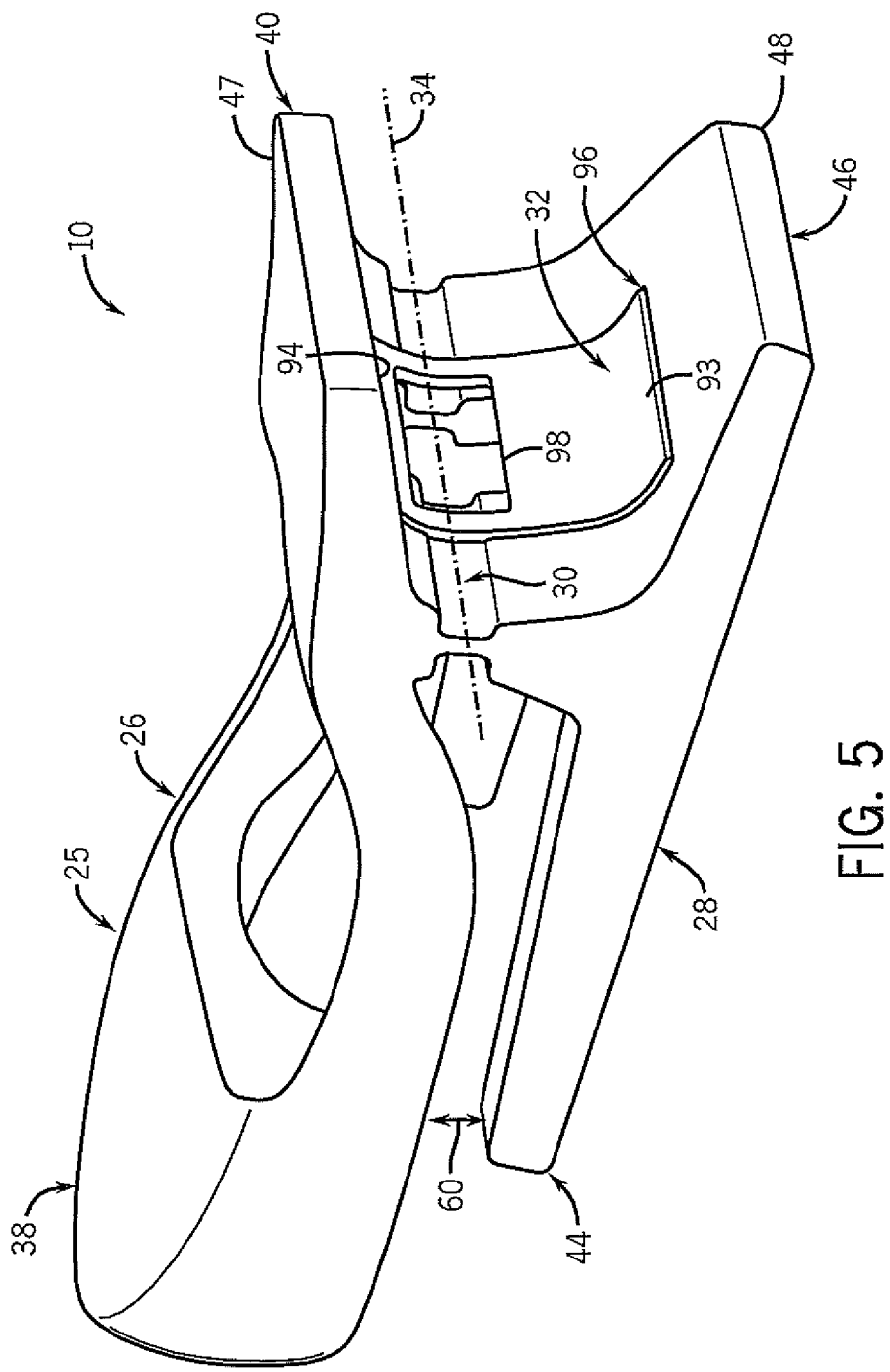
FIG. 5 is a perspective view of a third embodiment of the sensor having a living hinge, in accordance with an embodiment.

Turning now to FIG. 5, a perspective view of an embodiment of the sensor 10 including the biasing mechanism 32 is illustrated. In the depicted embodiment, the biasing mechanism 32 includes a flat spring 93 coupled to the sensor 10. For example, in the illustrated embodiment, the biasing mechanism 32, including the flat spring 93, is disposed in a first indentation 94 in the first segment 26 and a second indentation 96 in the second segment 28. The indentations 94 and 96 may facilitate alignment and retention of the biasing mechanism 32 relative to the living hinge 30.

Further, in certain embodiments, the biasing mechanism 32, including the flat spring 93, may include features conducive to flexing of the flat spring at or near the pivot axis 34. For example, in the illustrated embodiment, the flat spring 93 includes a cutout 98 proximate the pivot axis 34. The cutout 98 may encourage flexing and bending of the flat spring 93 at or near the pivot axis 34 and, thus, encourage the first segment 26 and the second segment 28 to pivot about the pivot axis 34 relative to one another. Further, the geometry and material of the flat spring 93 may be varied to accommodate various designs. For example, the flat spring 93 may include a metal (e.g., steel or aluminum), polymeric composition (e.g., polypropylene), or a similar material. Further, the size, shape, and number of cutouts 98 may be varied to influence the stiffness of the flat spring 93 and the resulting biasing force. For example, the size, number, and location of cutouts 98 may be increased or decreased to vary the force applied to open the sensor 10.

Figure 6:
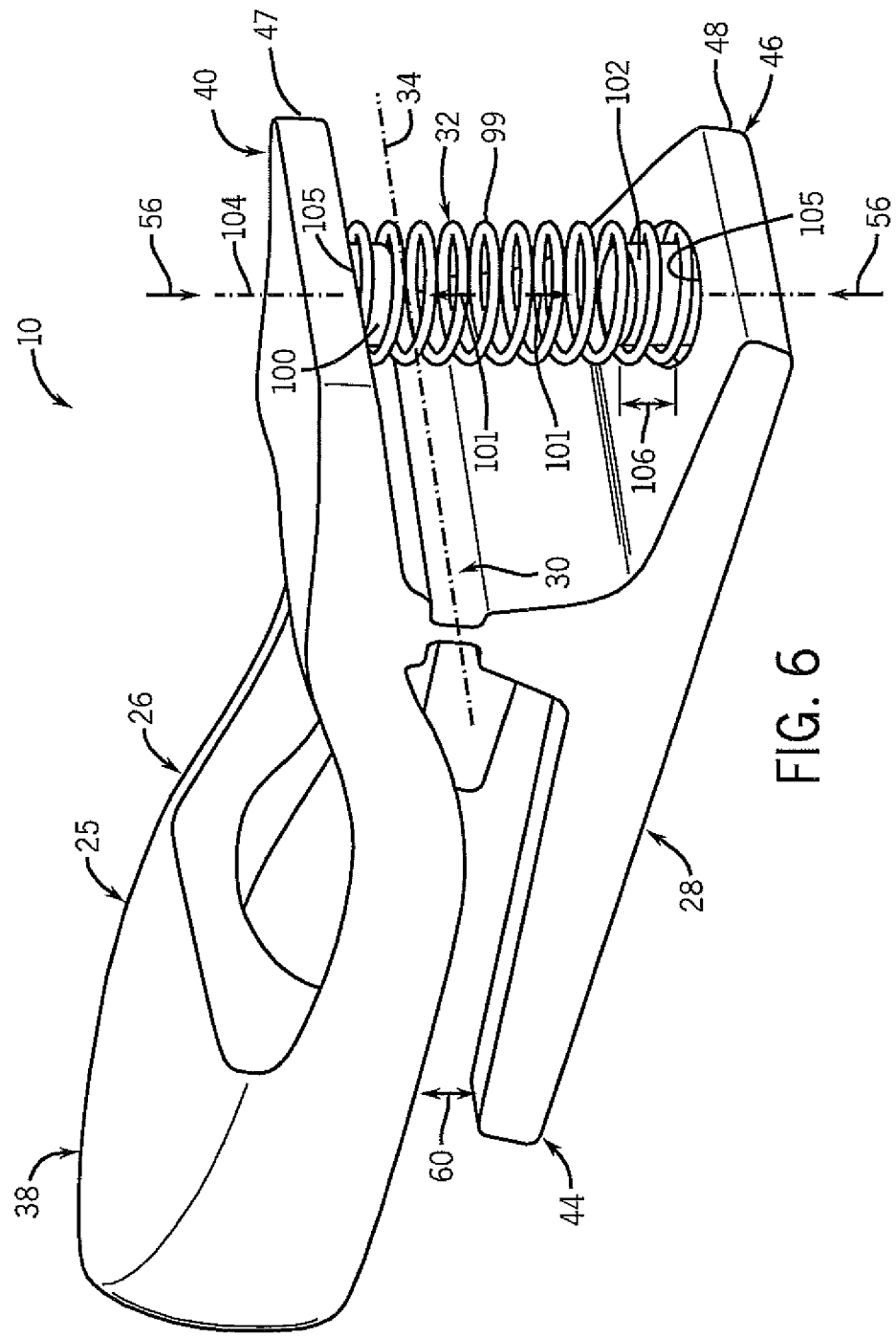
FIG. 6 is a perspective view of a fourth embodiment of the sensor having a living hinge, in accordance with an embodiment.

Turning now to FIG. 6, a perspective view of an embodiment of the sensor 10 including the biasing mechanism 32 is illustrated. In the depicted embodiment, the biasing mechanism 32 includes a compression spring 99 coupled to the sensor 10. For example, in the illustrated embodiment, the biasing mechanism 32 includes the compression spring 99 disposed about a first protrusion 100 on a face of the first segment 26 and about a second protrusion 102 on a face of the second segment 28. Accordingly, when an opening force is applied in the direction of the arrows 56 to squeeze the sensor 10 to the open position, the biasing mechanism 32 including a compression spring may generate a biasing force in the opposite direction (e.g., in the direction of arrows 101). The biasing force biases the sensor 10 to the closed position as discussed previously.

In an embodiment, the protrusions 100 and 102 are disposed along a protrusion axis 104. In one embodiment, the protrusion axis 104 is not parallel to the pivot axis 34. For example, in the illustrated embodiment, the protrusion axis 104 is generally perpendicular to and offset from the pivot axis 34. Each of the protrusions 100 and 102 may have axes that are coaxial or not coaxial. Further, the protrusions 100 and 102 may have a height 106 of approximately 0.1 inches, 0.2 inches, 0.4 inches, 0.5 inches or more. In operation and assembly, the protrusions 100 and 102 can facilitate alignment and retention of the biasing mechanism 32 relative to the living hinge 30.

In various embodiments, the protrusions 100 and 102 may be replaced or used in combination with indentations in the first segment 26 and/or the second segment 28. For example, the first and second segments 26 and 28 may include recesses 105 proximate the intersection of the protrusions 100 and 102 and the segments 26 and 28. In other words, the segments 26 and 28 may include a channel that surrounds the base of the protrusions 100 and 102, and that accepts at least a portion of the biasing mechanism 32. Further, an embodiment may include recesses 105 without employing a protrusion 100 or 102, i.e., the recesses 105 alone hold the biasing mechanism 32 in place. The recesses 105 may further promote alignment and retention of the biasing mechanism 32.

Figure 7:
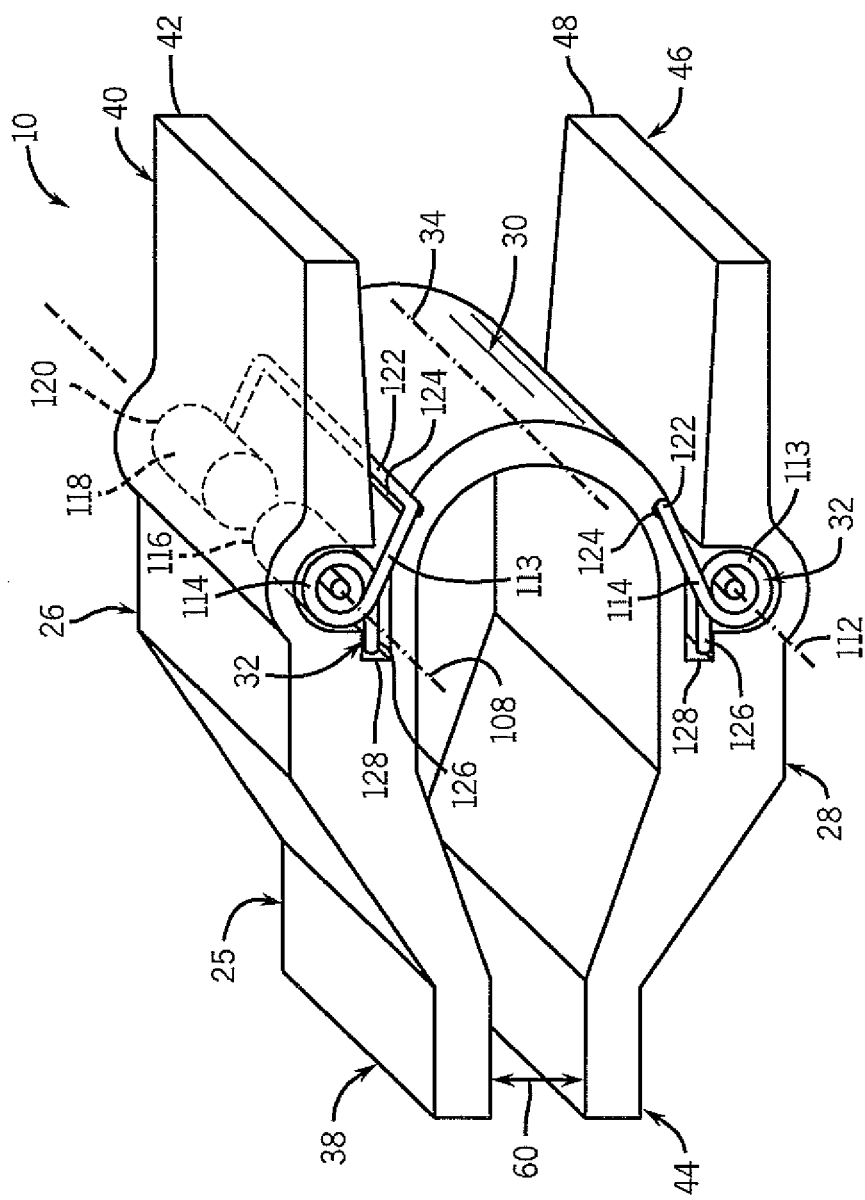
FIG. 7 is a perspective view of a fifth embodiment of the sensor having a living hinge, in accordance with an embodiment.

Turning now to FIG. 7, an embodiment of the sensor 10 including a plurality of biasing mechanisms 32 is illustrated. In the depicted embodiment, the sensor 10 includes two biasing mechanisms 32. A first biasing mechanism 32 may be disposed about a first axis 108, and a second biasing mechanism 32 may be disposed about a second axis 112. In the depicted embodiment, each of the first and second biasing mechanisms 32 and 110 include a double torsion spring 113. The first axis 108 and the second axis 110 may be parallel and offset from the pivot axis 34 of the living hinge 30. Each of the double torsion springs 113 may include a first end 114 having a coil disposed in a first indentation 116 and a second end 118 having a coil disposed in a second indentation 120. The first end 114 and the second end 116 may be coupled to one another via a leg 122 disposed in a channel 124 of the living hinge 30. The channels 124 may run parallel to the first axis 108 and the second axis 112. A second leg 126 may be disposed in an indentation 128 in the first and second segments 26 and 28. During assembly of the sensor 10, the biasing mechanisms 106 and 110 may be snapped into the indentations 116 and 120, the channels 124 and the indentation 128. Accordingly, in the depicted embodiment, the indentations 116, 120 and 128 and channels 124 may facilitate alignment and retention of the double torsion springs 113 relative to the living hinge 30.

In accordance with the previously discussed embodiments, the sensor 10 may be formed from various materials and by various processes. For example, the sensor 10 may be formed from a single type material or a combination of material types. In one embodiment, the first segment 26, the second segment 28 and the living hinge 30 may be formed from the same or similar material, such as polypropylene or other elastomers. In such an embodiment, these three components can be formed in a single-shot molding process that integrates each of the components into a single body that includes the first segment 26, the second segment 28 and the living hinge 30, and includes other features discussed previously. Alternately, the components can be formed separately, such as by independent molding processes, and subsequently coupled to one another, such as by an adhesive, a plastic weld, or other form of assembly.

In an embodiment, the first segment 26, the second segment 28 and the living hinge 30 may not be formed from the same material. For example, in one embodiment, the first segment 26 and the second segment 28 may be formed from a first material, such as polypropylene, and the living hinge 30 may be formed from a second material, such as a rubber thermoplastic elastomer (TPE). In such an embodiment, these three components can be formed in a two-shot molding process (i.e., a process that includes molding the components formed from the first material, followed by molding the components formed from the second material) that integrates each of the components in to a single body (e.g., body 25) that including the first segment 26, the second segment 28 and the living hinge 30, and any of the features discussed previously.

Further, forming the sensor 10 may include overmolding the sensor 10 with an additional material, such as a conformable or soft material (e.g., a material having a durometer below 40 Shore A). Overmolding may include disposing a material about the sensor that encapsulates or coats at least a portion of the segments 26 and 28, the living hinge 30, and/or other components of the sensor 10, such as the biasing mechanism 32, the emitter 22, the detector 24, and the cable 14. Overmolding may increase the durability of the sensor 10 by providing a flexible covering, and may enhance the overall appearance and ergonomics of the sensor 10.

Figure 8:
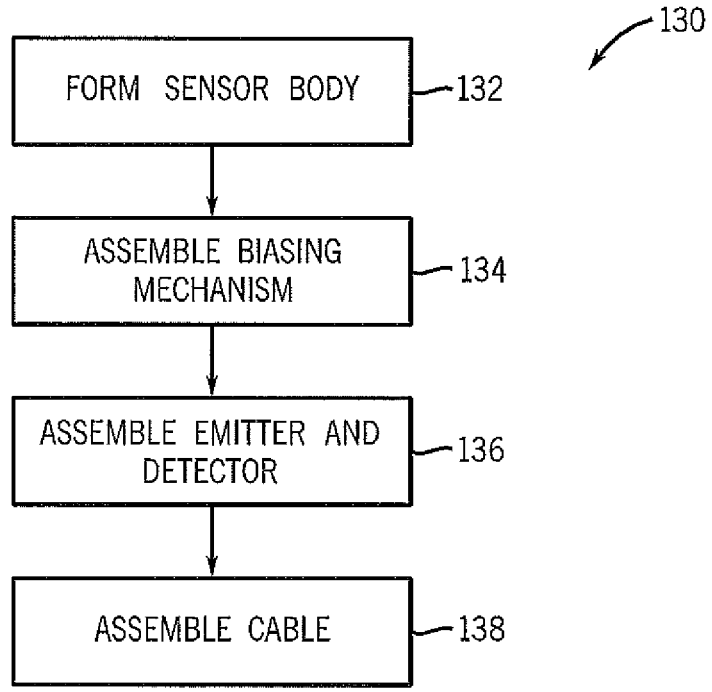
FIG. 8 is a flowchart that depicts a method for manufacturing a sensor having a living hinge, in accordance with an embodiment.

Turning now to FIG. 8, an embodiment of a method 130 for manufacturing the sensor 10 is depicted. The depicted method 130 may include forming the sensor body, as illustrated at block 132. Forming the sensor body (block 132) may include molding the first segment 26, the second segment 28, the living hinge 30, and other features as discussed above. In certain embodiments, forming the sensor body (block 132) may include a one-shot molding, a two-shot molding, overmolding and/or similar processes. However, in some embodiments, overmolding may be performed at a later stage in the manufacturing process.

The method 130 may also include assembling the biasing mechanism, as illustrated at block 134. Assembling the biasing mechanism (block 134) may generally include snapping, or otherwise positioning, the biasing mechanism 32 into place relative to the first segment 26, the second segment 28 and the living hinge 30. For example, a spring may be snapped into the slot 70, in the indentations 74, 80, 94, 96, 116, 118 and 128, around protrusions 100 and 102, in the hole 76, around the mandrel 84, in the channels 124, and the like, as discussed in the preceding embodiments.

The method 130 may also include assembling the emitter and the detector to the sensor 10, as illustrated at block 136. As discussed above, embodiments may include employing an adhesive, an interference fit, or other attachment technique to couple the emitter 22 and the detector 24 to the first segment 26 and the second segment 28, respectively. Further, the emitter 22 and detector 24 may be assembled prior to or after the sensor 10 is overmolded.

The method 130 may also include assembling the cable to the sensor, as illustrated at block 138. Assembling the cable 14 to the sensor 10 (block 138) may include making electrical connections between the cable and the sensing devices (e.g., the emitter 22 and the detector 24). For example, ends of the cable 14 may be soldered to complementary electrical leads, a strain relief snapped into place, or the like. It should be noted that in some embodiments, the cable 14 may be formed integrally with the sensor 10, and assembling the cable to 14 to the sensor 10 (block 138) may be performed prior to or integral with forming the sensor body (block 132). For example, the cable 14 may be coupled to the sensor 10 and/or the emitter 22, and molded as an integral component of the first segment 26, or integral to the overmolding of the sensor 10. As will be appreciated, the method 130 may include additional steps, and/or accomplish the method steps in various orders to achieve the desired result.

Figure 9:
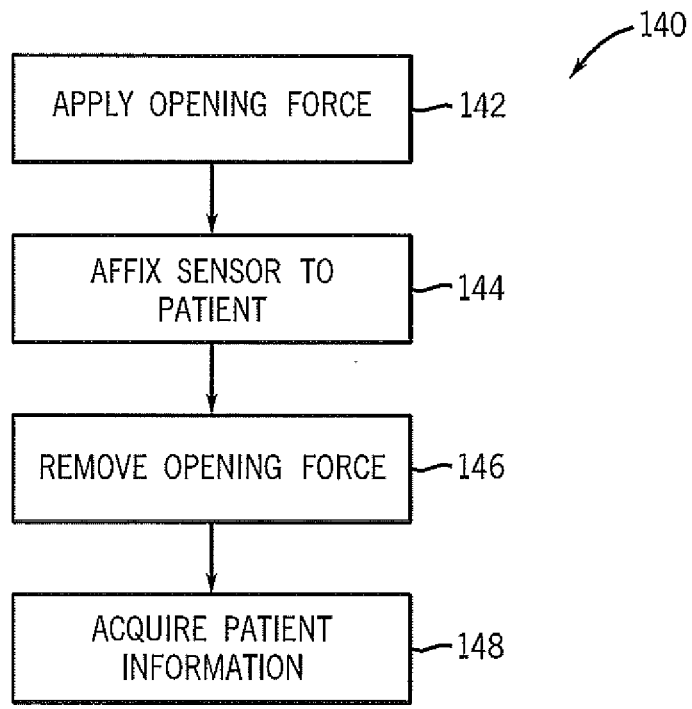
FIG. 9 is a flowchart that depicts a method for operating a sensor having a living hinge, in accordance with an embodiment.

Turning now to FIG. 9, an embodiment of a method 140 of operating the sensor 10 is illustrated. The method may include applying an opening force to the sensor, as illustrated at block 142. Applying an opening force (block 142) may include applying force in the direction of arrows 56 to increase the size of the gap 60 to bias the sensor 10 to the open position. The method 140 also includes affixing the sensor to the patient, as illustrated at block 144. For example, the first ends 38 and 44 of the sensor 10 may be disposed about the finger tip or other tissue of a patient, and the opening force removed, as illustrated at block 146. Removing the opening force may enable the sensor 10 to return to the closed position and be secured to the patient. As discussed previously, when the opening force is removed, the living hinge 30 and/or the biasing mechanism 32 may provide a sufficient biasing force to return the sensor 10 to the closed position and ensure the sensor 10 remains in contact with and attached to the patient. Accordingly, with the sensor 10 secured to the patient, the sensor 10 may be employed to acquire patient information, as illustrated at block 148. In other words, signals may be transmitted between the monitor 12 and the sensor 10 to acquire information relating to the patient. As will be appreciated, the method 140 may include additional steps, and/or accomplish the method steps in various orders to achieve the desired result.

While the medical sensors 10 discussed herein are some examples of integrally molded medical devices, other such devices are also contemplated and fall within the scope of the present disclosure. For example, other medical sensors and/or contacts applied externally to a patient may be advantageously applied using a sensor 10 having an integral living hinge 30. For example, devices for measuring tissue water fraction or other body fluid related metrics may utilize a sensor as described herein. Likewise, other spectrophotometric applications where a probe is attached to a patient may utilize a sensor as described herein.

While the disclosure may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosure as defined by the following appended claims.

What is claimed is:

1. A medical sensor assembly, comprising:
  a sensor body comprising:
    a first segment having a first protrusion;
    a second segment having a second protrusion;
    at least one sensing element disposed internally within the first segment or the second segment;
    a living hinge comprising a pivot axis, wherein the living hinge mechanically couples the first segment and the second segment, and is configured to enable the first segment and the second segment to pivot relative to one another generally about the pivot axis when a compression force is applied to the first protrusion and the second protrusion to move the first and second protrusions generally toward one another, and wherein the living hinge is configured to apply a first biasing force in the absence of the compression force to move ends of the first and second segments distal from the first and second protrusions generally toward one another; and
    a biasing member configured to generate a moment about the pivot axis of the living hinge, wherein the biasing member generates a second biasing force that moves the ends of the first and second segments generally toward one another.

2. The medical sensor assembly of claim 1, wherein the pivot axis is offset from a centerline of the sensor body.

3. The medical sensor assembly of claim 1, wherein the living hinge comprises a cross-sectional width that is generally less than the cross-sectional width of portions of the first segment and the second segment that are proximate the living hinge.

4. The medical sensor assembly of claim 1, wherein the biasing member comprises a torsion spring, a double torsion spring, a flat spring, a compression spring, a conical compression spring, or combinations thereof.

5. The medical sensor assembly of claim 1, wherein an axis of the biasing member is generally coaxial with the pivot axis of the living hinge.

6. The medical sensor assembly of claim 1, wherein an axis of the biasing member is generally not parallel to the pivot axis of the living hinge.

7. The medical sensor assembly of claim 1, comprising a mandrel configured to be disposed generally internal to a biasing member.

8. The medical sensor assembly of claim 1, wherein the body comprises a cutout that is configured to accept a biasing member.

9. The medical sensor assembly of claim 1, wherein the sensor body is formed from polypropylene.

10. The medical sensor assembly of claim 1, wherein the sensor body is formed from a first material and the living hinge is formed from a second material, and wherein the first material is different from the second material.

11. The medical sensor assembly of claim 10, wherein the first material comprises polypropylene and the second material comprises a thermoplastic elastomer.

12. The medical sensor assembly of claim 1, wherein the medical sensor assembly is configured for use in a pulse oximetry sensor.

13. The medical sensor assembly of claim 1, comprising an output cable coupled to a first end of the first segment, wherein the first end is configured to contact a patient.

14. The medical sensor assembly of claim 1, wherein the sensing element is an optical emitter configured to emit light in a red to infrared range or an optical detector configured to receive light in the red to infrared range.

15. The medical sensor assembly of claim 1, wherein the first and second protrusions extend outward from a location where the living hinge mechanically couples the first segment and the second segment.

16. The medical sensor assembly of claim 1, wherein the pivot axis of the living hinge is generally perpendicular to a longitudinal axis of the sensor body.

17. The medical sensor assembly of claim 1, wherein the at least one sensing element is disposed internally within an end of the first segment or the second segment, and the living hinge couples the first segment and the second segment at a location distal from the end.

18. A sensor system, comprising:
  a sensor assembly comprising:
    a sensor comprising a first sensing element and a second sensing element;
    a sensor frame configured to support the sensor, comprising:
      a first body portion configured to support the first sensing element internally within the first body portion, wherein the first body portion comprises a first protrusion;

a second body portion configured to support the second sensing element internally within the second body portion, wherein the second body portion comprises a second protrusion; and a living hinge mechanically coupling the first body portion and the second body portion, wherein the first body portion and the second body portion are configured to pivot relative to one another generally about a pivot axis of the living hinge when a compression force is applied to the first protrusion and the second protrusion to move the first and second protrusions generally toward one another, wherein the pivot axis of the living hinge is generally perpendicular to a longitudinal axis of the sensor frame, and wherein the living hinge is configured to apply a first biasing force in the absence of the compression force to move the first body portion and the second body portion toward one another; and at least one member configured to generate a moment about the pivot axis of the living hinge and generally bias a first end of the first body portion and a second end of the second body portion toward one another.

19. The sensor system of claim 18, wherein the member comprises a torsion spring, a double torsion spring, a flat spring, a compression spring, or a conical compression spring.

20. The sensor system of claim 18, wherein an axis of the member is generally coincident with the pivot axis of the living hinge.

21. The sensor system of claim 18, wherein the sensor frame is overmolded to enclose the first body portion, the second body portion, and the living hinge.

22. The sensor system of claim 18, comprising a monitor coupled to the sensor assembly.

23. The sensor system of claim 18, wherein the first and second sensing elements are optical emitters configured to emit light in a red to infrared range or optical detectors configured to receive light in the red to infrared range.

24. The sensor system of claim 18, wherein the first and second body portions are configured to support the first and second sensing elements internally within an end of the sensor frame, and wherein the living hinge mechanically couples the first and second body portions at a location of the sensor frame distal from the end of the sensor frame.

25. The sensor system of claim 18, wherein the living hinge comprises a first living hinge portion disposed on a first side of the at least one member, and a second living hinge portion disposed on a second side of the at least one member.

26. A method of manufacturing a sensor frame, comprising:

forming an integral sensor body having a first frame segment having a first protrusion, a second frame segment having a second protrusion, at least one sensing element disposed internally within the first frame segment or second frame segment, and a living hinge, wherein the first frame segment and the second frame segment are configured to pivot relative to one another generally about a pivot axis of the living hinge; and coupling at least one biasing mechanism to the first frame segment and the second frame segment, wherein the at least one biasing mechanism is configured to generate a moment about the pivot axis of the living hinge, and wherein the moment generally biases the first frame segment and second frame segment into a closed position, and wherein applying a compression force to the first protrusion and the second protrusion enables the first and second frame segments to pivot relative to each other into an open position, and wherein in the absence of the compression force the living hinge is configured to generate a biasing force configured to bias the first frame segment and the second frame segment into the closed position.

27. The method of claim 26, wherein the pivot axis of the living hinge is generally perpendicular to a longitudinal axis of the integral sensor body.

28. The method of claim 26, wherein the at least one sensing element is disposed within an end of the first frame segment or the second frame segment, and the living hinge couples the first frame segment and the second frame segment at a location of the integral sensor body distal from the end.

29. The method of claim 26, wherein the integral sensor body is overmolded to enclose the first frame segment, the second frame segment, and the living hinge.

* * * * *